(12) United States Patent
Janzen et al.

(10) Patent No.: US 10,184,611 B2
(45) Date of Patent: Jan. 22, 2019

(54) DETECTING FLUID PROPERTIES OF A MULTIPHASE FLOW IN A CONDENSATE DRAIN

(71) Applicant: GESTRA AG, Bremen (DE)

(72) Inventors: Sergej Janzen, Bremen (DE); Holger Schroter, Achim (DE); Jurgen Klattenhoff, Delmenhorst (DE)

(73) Assignee: GESTRA AG, Bremen (DE)

( * ) Notice: Subject to any disclaimer, the term of this patent is extended or adjusted under 35 U.S.C. 154(b) by 151 days.

(21) Appl. No.: 14/440,912

(22) PCT Filed: Nov. 7, 2013

(86) PCT No.: PCT/EP2013/073304
§ 371 (c)(1),
(2) Date: Jul. 31, 2015

(87) PCT Pub. No.: WO2014/072430
PCT Pub. Date: May 15, 2014

(65) Prior Publication Data
US 2016/0290560 A1  Oct. 6, 2016

(30) Foreign Application Priority Data
Nov. 9, 2012 (DE) .................. 10 2012 220 505

(51) Int. Cl.
*G01F 1/32* (2006.01)
*F16T 1/48* (2006.01)
(Continued)

(52) U.S. Cl.
CPC ............... *F16T 1/48* (2013.01); *F28B 11/00* (2013.01); *G01F 1/00* (2013.01); *G01F 1/28* (2013.01);
(Continued)

(58) Field of Classification Search
None
See application file for complete search history.

(56) References Cited

U.S. PATENT DOCUMENTS

| | | | |
|---|---|---|---|
| 4,248,098 A | 2/1981 | Sawayama et al. | |
| 4,526,040 A * | 7/1985 | Matsubara | ............ G01F 1/3245 73/861.24 |

(Continued)

FOREIGN PATENT DOCUMENTS

| | | |
|---|---|---|
| CN | 1275196 A | 11/2000 |
| CN | 101189493 A | 5/2008 |

(Continued)

OTHER PUBLICATIONS

Japan Patent Office, translation of Official Action issued in Patent Application No. 2015-541138, dated May 31, 2016.
(Continued)

*Primary Examiner* — Harshad R Patel
(74) *Attorney, Agent, or Firm* — Thompson Hine LLP

(57) ABSTRACT

Flow sensors for, and a method of monitoring, a condensate drain. The method includes a) providing a flow sensor for detecting flow properties in a pipe and/or fitting carrying a medium, b) detecting a vibration behavior by means of a vibration converter at a measurement location provided on the flow sensor, and c) electronically evaluating the vibration behavior of a vibration body, wherein at the measurement location vibrations of a first region of the vibration body and a second region of the vibration body are recorded. The first region of the vibration body is provided at least partially in or adjacent to the flow of the medium, and the second region of the vibration body is outside the flow.

19 Claims, 7 Drawing Sheets

(51) Int. Cl.
*F28B 11/00* (2006.01)
*G01P 5/24* (2006.01)
*G01F 1/00* (2006.01)
*G01F 1/28* (2006.01)
*G01N 29/032* (2006.01)
*G01N 29/36* (2006.01)
*F28F 17/00* (2006.01)
*F28B 9/08* (2006.01)

(52) U.S. Cl.
CPC .......... *G01N 29/032* (2013.01); *G01N 29/36* (2013.01); *G01P 5/24* (2013.01); *F28B 9/08* (2013.01); *F28F 17/005* (2013.01); *F28F 2265/00* (2013.01)

(56) References Cited

U.S. PATENT DOCUMENTS

| | | | | |
|---|---|---|---|---|
| 4,706,503 | A * | 11/1987 | Kamentser | G01F 1/3209 73/861.24 |
| 5,869,772 | A * | 2/1999 | Storer | G01F 1/3263 73/861.22 |
| 6,003,384 | A * | 12/1999 | Frohlich | G01F 1/3263 73/861.22 |
| 6,332,494 | B1 * | 12/2001 | Bodas | F28B 9/10 165/111 |
| 6,352,000 | B1 | 3/2002 | Getman et al. | |
| 8,250,924 | B2 * | 8/2012 | Hedtke | G01H 11/08 73/861.24 |
| 8,448,515 | B2 * | 5/2013 | Orleskie | G01F 1/34 73/861.42 |
| 2002/0174728 | A1 | 11/2002 | Beresford et al. | |
| 2008/0307882 | A1 | 12/2008 | Schroter et al. | |
| 2009/0013798 | A1 * | 1/2009 | Hocker | G01F 1/36 73/861.03 |
| 2011/0107847 | A1 * | 5/2011 | Strom | G01F 1/3209 73/861.24 |
| 2011/0154913 | A1 * | 6/2011 | Konyukhov | G01F 1/3209 73/861.24 |
| 2011/0314934 | A1 * | 12/2011 | Limacher | G01F 1/3218 73/861.24 |

FOREIGN PATENT DOCUMENTS

| | | |
|---|---|---|
| DE | 2623956 A1 | 12/1977 |
| DE | 201196 | 7/1983 |
| DE | 3301855 A1 | 7/1984 |
| DE | 3936026 A1 | 5/1991 |
| DE | 4216623 C2 | 11/1993 |
| DE | 4303798 A1 | 8/1994 |
| JP | 000H01158297 A | 6/1989 |
| JP | 01182699 A | 7/1989 |
| JP | 01210700 A | 8/1989 |
| JP | 10252987 A | 9/1989 |
| JP | 000H04151520 A | 5/1992 |
| JP | 2002522781 | 4/2000 |

OTHER PUBLICATIONS

International Searching Authority, International Search Report and Written Opinion issued in corresponding Application No. PCT/EP2013/073304, dated Nov. 13, 2014, 9 pages.
German Patent Office, Examination Report issued in corresponding Application No. 102012220505.5, dated Jul. 8, 2013, 6 pages.
State Intellectual Property Office of People's Republic of China, first Office Action issued in Application No. 201380069992.7 dated Feb. 3, 2017.
Patent Office of the People's Republic of China, Search Report issued in Application No. 201380069992.7 dated Jan. 23, 2017.

* cited by examiner

DETECTING FLUID PROPERTIES OF A MULTIPHASE FLOW IN A CONDENSATE DRAIN

BACKGROUND

The invention concerns a method of monitoring a condensate drain, and a flow sensor for detecting flow properties in a pipe and/or a fitting carrying a medium, in particular a condensate drain, and a monitoring device for monitoring at least one condensate drain.

Condensate drains are usually employed in installations in the chemical, pharmaceutical and energy-technology industries in order to drain from the installation a condensate which is formed in vapor lines or containers or in shaping processes. In that case drainage of the condensate must be effected at a given moment in time in order to prevent a so-called water hammer and to provide for effective use of energy. Such a water hammer occurs when vapor is introduced into a liquid at a lower temperature or occurs in such a liquid. In addition the condensate drain should prevent vapor from being discharged in the event that no condensate is present.

In such installations, wear phenomena, contamination and/or deposits can occur, for example, by virtue of erosion due to magnetite formation. That can result in leakages or blockages in condensate drains used in the installations. In that respect, it is not possible to see whether the condensate drain is or is not operating from the exterior, that is to say from outside the installation or the pipes and/or the condensate drain. The operability of the condensate drains used is to be checked in a method of monitoring condensate drains. In that respect, it is necessary to clearly establish whether the condensate drain is functioning in fault-free fashion and whether, in the case of faulty functioning, a leak or a blockage occurs. That is necessary as, for example, blocking condensate drains can lead to considerable reductions in the output of the installation, and leaky condensate drains result in vapor losses which in turn represent a considerable economic loss. In addition, a rise in pressure in condensate networks, that is to say in a system with a plurality of condensate drains, is to be expected. Difficulties caused thereby in regard to drainage can then occur at a number of condensate drains in the installation. In addition, there can be a condensate build-up, which can cause water hammers and can also lead to serious damage in the vapor-condensate system. Usually, a proportion of defective condensate drains of an order of magnitude of 15 to 25% is to be expected in installations without regular checking or maintenance. That failure rate can be markedly reduced by regular checks to be performed.

A number of methods of monitoring a condensate drain are already known. The condensate drains can be checked, for example, by means of sight glasses, by level measurement, and by means of sound measurement. A disadvantage with the specified methods is that the operability of the condensate drain can only be estimated.

The methods based on sound measurement rely on detection of the solid-borne sound which is emitted from the surfaces of the housings of the condensate drains. To be able to assess the operating mode of the condensate drain, the detected intensity of the solid-borne sound is shown on a display device or compared to previously recorded reference data.

In that respect, manual checking of each individual condensate drain is usually required, and that involves a great deal of time and effort in larger installations. Under some circumstances, that leads to relatively long checking intervals so that faults in the condensate drain system cannot be immediately detected and removed.

Usually mechanical contact with the condensate drain being investigated is required to detect solid-borne sound. Governed by the structure involved, the measurement results are relatively closely related to the contact pressure force and the contact pressure angle of the measuring sensor, so that any change in one of those parameters can lead to a inaccurate measurement result. In addition, the contact location must be defined as accurately as possible.

By evaluating exclusively the sound intensity in the ultrasound range, it is not possible to accurately establish whether the condensate drain is just draining or has a water hammer by virtue of damage. That case does not afford clear ascertainment of the working condition.

SUMMARY

The object of the present invention is therefore that of eliminating or at least reducing the described disadvantages. In particular, the invention seeks to provide a method of monitoring a condensate drain or suitable apparatuses for that purpose, which permits or permit different properties of the medium or the mode of operation of the condensate drain to be reliably and precisely determined.

According to the invention, therefore, there is proposed a method of monitoring a condensate drain. The method includes the steps of: a) providing a flow sensor for detecting flow properties in a pipe and/or fitting carrying a medium, wherein the medium is in the form of a multi-phase flow, b) detecting a vibration behavior at a measurement location provided on a vibration body of the flow sensor by means of the vibration converter, and c) electronically evaluating the vibration behavior of a vibration body.

In that case, at the measurement location, vibrations of a first region of the vibration body, which is provided at least partially in a flow of the medium, and a second region of the vibration body, that is outside the flow, are recorded. The vibrations can be detected at the second region of the vibration body, for example by means of a piezoelectric element, laser vibrometer, or microphone.

The term condensate drain is also used hereinafter to denote a condensomat and/or a regulating fitting which drains off a condensate which forms in vapor lines or containers or shaping processes. To monitor such a condensate drain and therefore to check the operability thereof, there is provided a flow sensor for detecting flow properties in a pipe and/or fitting carrying a medium. In that case, the medium is in the form of vapor or steam, condensate, water and/or air, in particular in the form of a multi-phase flow. In that respect, the vibration body is at least partially used in a pipe cross-section and/or fitting cross-section through which the medium flows. In that case, the medium flows around the vibration body or the vibration body, which is arranged near the flow, in particular at the flow surface, so that it at least partially touches the flow. The vibration body is caused to vibrate by the flow of the medium. The vibration behavior resulting therefrom is detected by means of the vibration converter and representative signals of the vibration behavior are produced. In that respect, the detected vibration behavior includes, in particular, detection of the amplitude and frequency of the vibration. The vibration amplitude and frequency detected in that way is outputted to the measurement location by way of an electric signal of the vibration converter. In that case, the vibration converter can be, for example, of such a configuration that the vibrations are detected by a piezoelectric sensor, a microphone, or by way of a laser vibrometer.

Preferably, in accordance with a development of the method according to the invention, in-phase vibrations and out-of-phase vibrations of the two intercoupled regions of the vibration body are recorded at the measurement location. Excitation of the vibration body is preferably effected by means of the first region of the vibration body, that at least partially projects into the flow of the medium, wherein both the first region disposed in the flow and also the second region outside the flow are excited to vibrate. By virtue of an elastic coupling of the two regions of the vibration body with each other and with a main body of the flow sensor, the two regions of the vibration body perform in-phase vibrations and out-of-phase vibrations, also referred to as co-directional and counter-directional vibrations. In that case, the vibration body is designed so that the in-phase and out-of-phase vibrations occur simultaneously at different frequencies. The term co-directional vibrations or in-phase vibrations of the two regions, starting from the connecting region of the two regions of the vibration body, that preferably extend in opposite directions, are to be interpreted as meaning vibrations in which the two intercoupled regions of the vibration body move in the same direction. The term out-of-phase vibrations is to denote vibrations of the two regions in which they vibrate in opposite directions, also starting from the connecting region of the two regions of the vibration body. Preferably by frequency analysis, also referred to as spectral analysis, of the vibration behavior of the vibration body, preferably two resonance frequencies occurring in the vibration body and their amplitudes of the in-phase and out-of-phase vibrations are simultaneously detected.

By virtue of recording and analysis of the vibration behavior of the vibration body, comprising two elastically coupled regions which are preferably disposed in two different media, wherein the first region is arranged in the multi-phase flow and the second region of the vibration body is preferably arranged in the ambient air, amplitude and frequency of two resonance locations are detected. In that way, it is possible to detect mass transport processes in respect of multi-phase flows, whereby it is possible to determine the condensate level and its flow speed as well as the level of the vapor and its flow speed. Operability, pressure stage, amount of condensate and vapor loss amount of a condensate drain can be clearly ascertained by means of the stored reference data set. Ambiguous results are excluded by the combination of the amplitude and frequency of the two resonance locations. It is possible to determine the operability of the condensate drain by way of that combination or properties of the flow.

Preferably the flow sensor is provided between the pipe and the condensate drain, and is in particular connected releasably to the pipe and the condensate drain by means of a first flange associated with the pipe and a second flange associated with the condensate drain. When the flow sensor is provided at that position, it is advantageous for a foreign sound which occurs in such installations, for example originating from a condensate drain, to be so slight that it influences the measurements at that location scarcely to almost not at all. In that respect the flow sensor can be clamped, for example, between the two flanges and the two flanges can be screwed together so that the flow sensor is fixedly arranged between the two flanges.

In an embodiment to evaluate the flow behavior according to step c), reference measurements are carried out and/or data sets are produced thereby, which are used for comparison with the data measured at the measurement location. The data sets in that case are of such a nature that certain properties of the flow, such as for example the condensate amount, the loss amount, and the flow speed, are predetermined for different operating conditions. Thus, for example, when measuring amplitude and frequency, and with a given level and a mean flow speed with a given condensate amount, it is possible to infer an operating condition which is known for those regions and thus the operability of the condensate drain. The use of such a system makes it possible to effect functional checking independently of drain type. Thus, independently of the downstream-connected drain type, the system can be universally employed as a drain diagnosis system.

Preferably when monitoring a condensate drain in accordance with an embodiment for evaluation of the flow behavior in accordance with step c), on the basis of data sets produced by means of previously implemented reference measurements, the data measured at the measurement location are compared to the data sets. That permits simple, and at the same time, fast evaluation of the measured data, and reliable determination by way of the values to be ascertained in connection with the vibration behavior of the vibration body, with which it is possible to provide information about the operability of the condensate drain. The comparison between the measured data and the previously produced data sets is preferably effected by means of an electronic evaluation device in which the previously produced data sets are stored at the same time.

In a preferred embodiment the evaluation according to step c) is effected by way of an electronic evaluation device, such as, for example, an artificial neural network (ANN), fuzzy logic, channel relationships methods or principal component analyses (PCA).

A further development of the method according to the invention provides that, for evaluation of the flow behavior by means of the electronic evaluation device in accordance with step c), the amplitudes and the resonance frequencies of the detected in-phase and out-of-phase vibrations of the preferably two regions of the vibration body are determined. On the basis of the magnitude of the amplitudes and on the basis of the different resonance frequencies produced by the in-phase and out-of-phase vibrations at the vibration body, it is possible, by comparison with the data sets already ascertained, to implement an evaluation operation by which it is possible to provide information relating to given values reflecting the operating condition of the condensate drain, like, for example, operability, amount of condensate, pressure stage and vapor loss amount of the condensate drain.

Preferably, to evaluate the flow behavior in accordance with step c), the amplitudes and their resonance frequencies of the detected in-phase and out-of-phase vibrations of the two regions of the vibration body are determined by way of a frequency analysis operation, preferably a Fourier analysis. That kind of frequency and amplitude ascertainment provides a simple possible way of representing the vibrations which occur of the vibration body excited by the flow. In particular, the frequencies of the individual vibrations and their amplitudes can be advantageously ascertained by means of the Fourier analysis operation.

Preferably, upon evaluation in accordance with step c), a relationship is produced between, on the one hand, an operability, a pressure stage, a condensate amount and a vapor loss amount, and on the other hand, a resonance frequency and an amplitude, preferably two resonance frequencies and their amplitudes, at the flow sensor. The current operating condition of a drain can be ascertained by that relationship from a vibration spectrum.

In a further embodiment, the condensate level of the medium is determined by way of a dependency of the resonance frequency and amplitude of the in-phase and out-of-phase vibration on a damping. If, in the evaluation of a water-vapor flow, a change in the resonance frequency and amplitude is to be found, the condensate level can be ascertained therefrom by means of suitable evaluation. For example a change in the amplitude and a reduction in the resonance frequency of the in-phase and out-of-phase vibration, on the assumption of a constant density of the medium, signify more accentuated damping as a consequence of a rise in level in the conduit.

Preferably, the condensate level in the multi-phase flow, and damping of the medium, resulting therefrom, is determined by way of a dependency of the variation in the resonance frequency and amplitude of the in-phase and out-of-phase vibration at the vibration body. In the variation in the resonance frequency and the amplitude of the in-phase and out-of-phase vibration of the two regions of the vibration body, it is possible to deduce, in particular, a measurement in respect of the condensate level in the multi-phase flow and the damping linked thereto of the medium flowing through the fitting, which is preferably in the form of a multi-phase flow. The damping of the medium acts directly on the vibration behavior of the first region of the vibration body, which at least partially projects into the flow and thus also into the condensate. In the case of the coupled vibration body according to the invention, that action leads to a simultaneous change in amplitude and frequency of the in-phase and out-of-phase vibration of the two regions.

Preferably, a flow speed of the medium, preferably the multi-phase flow, is determined by way of a dependency of the amplitude and resonance frequency of the in-phase and out-of-phase vibration on the flow speed and/or the damping. If, for example, the amplitude of the in-phase and out-of-phase vibration rises with a constant resonance frequency, that means, on the assumption of a constant density of the medium, that the flow speed, and thus also the through-flow amount, is rising.

In a further embodiment, the pressure stage is determined by way of a dependency of the resonance frequency and amplitude of the in-phase and out-of-phase vibration on the damping. With different pressure stages, the medium changes its property and in particular its density. The damping in turn changes as a result. The respective pressure stage can be established on the basis of the dependency of amplitude and frequency on damping.

In a further embodiment, the density of the medium is determined by way of a dependency of the resonance frequency and amplitude of the in-phase and out-of-phase vibration on the damping. On the basis of the dependency of the amplitude and frequency on the damping, it is possible to establish the density of the respective medium.

Preferably, according to a development of the method according to the invention, a temperature, preferably of the medium and/or in the region of the pipe and/or condensate drain, is measured. By means of the temperature measurement it is possible to provide fundamental information relating to the operating condition or the operability of the condensate drain in connection with the data recorded at the flow sensor. By means of the temperature measurement, which is preferably effected in the region of vibration measurement, it is possible, in particular, to ascertain whether there is a congestion at the condensate drain, by virtue of a defect at the drain, or whether the condensate drain is closed. In that respect, what is crucial for determining the operating condition of the drain is the indication as to whether the ascertained temperature is falling below a given temperature range within which the condensate drain typically operates. On the basis of the measured temperature and the flow measurement, which is performed at the same time, it is preferably possible with a high degree of certainty to determine whether there is a congestion at the condensate drain or whether the installation portion is shut down.

A further aspect of the invention concerns a flow sensor for detecting flow properties in a pipe and/or fitting carrying a medium. In that case, the flow sensor comprises a main body, an opening which is arranged within the main body and which is of a flow cross-section adapted for the medium to flow therethrough, a vibration body which projects in adjacent relationship to the flow cross-section or into the flow cross-section, and a vibration converter provided on the vibration body for converting the mechanical vibrations into electrical signals. According to the invention, the flow sensor is distinguished in that the vibration body has a first region provided at least partially in the flow cross-section of the medium which is in the form of a multi-phase flow, and a second region provided outside the flow cross-section, wherein the first and second regions form a coupled system and the vibration body is adapted at the measurement location to record vibrations of the first region and the second region of the vibration body.

The main body and the vibration body are in that case connected together. Preferably, the vibration body has a first region provided at least partially in the flow cross-section and a second region provided outside the flow cross-section, wherein the first and second regions form a coupled system. The amplitude and frequency of the in-phase and out-of-phase vibration of the two regions are simultaneously detected by the coupled system at only one measurement location, preferably provided at the second region. That excludes ambiguous results and a clear association of the results is thus possible.

Preferably, the vibration body is so designed that, upon excitation of only a first region of the vibration body, which preferably at least partially projects into the flow, co-directional vibrations, also referred to as in-phase vibrations, and counter-directional vibrations, also known as out-of-phase vibrations, are produced by the two intercoupled regions of the vibration body. The in-phase and out-of-phase vibrations produced, as stated in greater detail hereinbefore in relation to the method, can be recorded at the measurement location at the second region outside the flow.

The flow cross-section is defined by the opening in the main body. It has a cross-section which only slightly influences the flow of the medium. Vibrations are excited by that flow of the medium, and they are detected by the vibration converter. The vibration body is at least partially arranged in the flow to generate the vibrations.

Preferably, the vibration body is of a bar-shaped configuration and/or the main body is annular. The bar-shaped vibration body can thus be based on general calculation theories in respect of the natural vibration of a bar. The two regions of the vibration body are preferably in the form of bending beams of preferably circular cross-section, which are fixedly connected together by way of a connecting region which is enlarged in cross-section in comparison with the two regions. Preferably, the first and second regions are so arranged at the connecting region that they can preferably vibrate unimpededly transversely relative to the direction in which they extend. In that respect the vibration body is formed and/or made in particular from a material with a high modulus of elasticity. As a result, it is stiff and is thus suitable for being caused to vibrate by the flow. It is an advantage in the case of an annular main body that it can be adapted, for example, to a pipe cross-section and can thus be integrated into any installation without any problem.

Another embodiment of the flow sensor according to the invention provides that the flow body has a mounting shoulder or collar which subdivides its two regions, and which is fixedly disposed on the main body, and is adapted to elastically couple the two regions of the vibration body to each other and to the main body. Preferably, the mounting shoulder for the vibration body is of a circular cross-section which is enlarged in diameter in comparison with the two regions of the vibration body. The mounting shoulder or collar forms the connecting region for the first and second regions of the vibration body, by way of which the vibrations can be passed to and fro unimpededly between the first and second regions. The material thickness of the mounting shoulder and its diameter are, in particular, in a predetermined relationship with the lengths and the diameters of the two regions of the vibration body, that are preferably in the form of cylindrical bending beams. As a result, upon excitation of at least one bar-shaped region of the vibration body, in particular transversely relative to the direction in which it extends, a diaphragm vibration is produced at the mounting shoulder and thus permits in-phase and out-of-phase vibration of the two interconnected regions of the vibration body.

The main body has a through passage for the vibration body, by way of which preferably a first region projects into the flow cross-section. The through passage, whose cross-section is basically larger than the region of the vibration body that at least partially projects into the flow, is in the manner of a stepped bore and has two portions of cross-sections of different sizes. The portion of larger cross-section is associated with the periphery of the main body, whereby a step with a contact surface is provided on the main body on which the mounting shoulder rests only in respect of a given proportion of its surface area. A large part of the mounting shoulder is freely vibrating, whereby diaphragm vibration is possible at the vibration body, and thus co-directional and counter-directional resonance vibrations of the regions of the vibration body can occur.

A preferred development of the vibration body provides that the vibration body has a preferably cylindrical mounting shoulder or collar, at which a respective bending beam of a preferably circular cross-section is arranged at mutually opposite sides. The vibration body has two, preferably coaxially arranged, bending beams fixedly connected together by way of the mounting shoulder or collar. The bending beams are preferably of a circular cross-section, and are arranged on mutually opposite side faces of the mounting collar or shoulder. The bending beams are preferably of equal diameters. In a preferred configuration, the diameter of the mounting shoulder or collar is about twice as large as the diameters of the two bending beams. The cylindrical mounting shoulder or collar rests with a face on a contact surface of the main body. One of the bending beams is arranged to project approximately perpendicularly at that face, and forms the first region of the vibration body, which at least partially projects into the multi-phase flow.

In a further embodiment, the diameter of the mounting shoulder or collar in relation to the material thickness of the mounting shoulder or collar is in a relationship in the region of 5 to 9, preferably in the region of 6 to 7. In addition the diameter of the mounting shoulder or collar relative to the diameter of the respective bending beam of the flow sensor is in a relationship in the region of 1.5 to 3.5. In a preferred configuration the relationship of the diameter of the mounting shoulder or collar to the diameter of the respective bending beam is in the range of between 2 and 3. Preferably the length of the respective bending beam relative to the diameter of the bending beam is in a relationship in the region of 2 to 6, particularly preferably a relationship in a range of between 3 and 4. The above-specified relationships of the dimensions of the mounting collar or shoulder and the bending beams relative to each other provides for an optimum vibration behavior of the vibration body according to the invention, and thus provides for reliably determining the measurement data to be ascertained.

In a preferred embodiment, the flow cross-section is adapted to the cross-section through which the medium flows. Adaptation of the flow cross-section avoids additional turbulence phenomena at the transitional location between the pipe conduit and the flow sensor. Thus a vibration is excited solely by the medium flowing around the vibration body in the flow sensor. Suitable adaptation of the vibration body ensures that the mode of operation of a drain is not adversely affected by the flow sensor.

Preferably, the flow sensor is adapted to carry out a method as described hereinbefore. The operability of a condensate drain can thus be monitored by means of such a flow sensor.

In addition, according to the invention, there is proposed a monitoring device for monitoring at least one condensate drain for draining off a condensate. In that case, the monitoring device includes at least one flow sensor with a vibration converter and an electronic evaluation means. The flow sensor, in particular according to one of the preceding embodiments, is releasably connected to the pipe and/or condensate drain, in particular according to one of the preceding embodiments, which is releasably connected to the pipe and/or condensate drain. In that case, the flow sensor is arranged adjacent to the pipe and/or condensate drain. Hereinafter, the reference to adjacent is used to mean that the flow sensor is arranged, for example, adjoining the pipe and/or the condensate drain, but at least in the very close proximity of or tightly thereto.

Preferably the flow sensor is arranged between the pipe and the condensate drain. In that way the recording of foreign sound, for example produced by and coming from the condensate drain, by the vibration body is avoided.

In a further embodiment, the flow sensor is releasably connected to the pipe and the condensate drain by means of a first flange associated with the pipe and a second flange associated with the condensate drain. In that way, the flow sensor can be replaced at any time simply and without complication for, for example, maintenance operations or in the event of a defect. In addition, there is no need either for an additional connecting device for fitting the flow sensor into the installation, as the flanges which are already present can be used, nor does the flow sensor have to be manually held in a predetermined position.

Preferably, the flow sensor is provided between the pipe and the condensate drain, preferably upstream of the condensate drain, and is in particular connected releasably to the pipe and the condensate drain by means of a first flange associated with the pipe and a second flange associated with the condensate drain. When providing the flow sensor at that position, which is decoupled in respect of solid-borne sound, it is advantageous that a foreign sound which occurs in such installations due for example to vibration of the pipes and/or the condensate drain is so slight that it influences the measurements at that location scarcely to almost not at all. In that case, the flow sensor can, for example, be clamped between the two flanges and the two flanges can be screwed together so that the flow sensor is arranged fixedly between the two flanges.

Another development of the monitoring device according to the invention provides that there is provided at least one temperature measuring device for detecting a temperature, preferably of the medium and/or in the region of the pipe and/or condensate drain, preferably in the region of vibration measurement. Preferably, temperature measurement is effected in the region of the condensate drain by means of the temperature measuring device, which preferably has a temperature sensor. By way of the preferably continuously queried temperature, it is possible to provide information as to whether an unwanted congestion of condensate has occurred in the region of the condensate drain by virtue of a defective component, or whether the condensate drain is closed. By means of the temperature measuring device, it is easily possible to establish whether the measured temperature is falling below a given temperature range within which the condensate drain typically operates. On the basis of the measured temperature and the flow measurement, which is performed at the same time, it is preferably possible to determine with a high degree of certainty whether there is a congestion at the condensate drain or whether that installation portion is shut down.

In a preferred embodiment, the monitoring device has an electronic evaluation device which is adapted for evaluating the signals of the vibration converter and for comparison of the incoming signals of the vibration converter of the flow sensor with a data set stored in the electronic evaluation device.

In that case, the data set comprises in particular the ascertained reference data. From that data set and the incoming signal, the electronic evaluation device acquires information about the properties of the flow and thus demonstrates the operating condition of the condensate drain. Preferably, a plurality of data sets are stored in the electronic evaluation device, which involve the relevant data like, for example, operability, condensate amount, vapor loss amount and pressure stage, preferably of all operating conditions of a drain with the associated sensor data like, for example, amplitude and frequency of the in-phase and out-of-phase vibration, and temperature. In addition, the electronic evaluation device is adapted to compare the measured data to the stored data sets. If the measured data, for example, should not exactly match a stored data set, it is possible to effect interpolating determination of the relevant data by way of the evaluation device.

Preferably, a further configuration of the monitoring device according to the invention provides that the evaluation device is a component part of an electronic control unit and/or the control unit is in signal-conducting communication with at least one energy generating device, preferably a thermogenerator, and a communication unit for data transfer. The electronic control unit is preferably coupled to an energy generating device and a communication unit, and is connected by way of a cable or wireless data connection to the flow sensor. A sensor node is preferably provided at each measurement location by means of the control unit, the energy generating device and the communication unit. Such a sensor node communicates with a portable query and output device or a stationary base station by way of the communication unit, preferably wirelessly directly and/or by way of other sensor nodes. Querying of the measurement data is possible, by way of the portable query and output device, from the various sensor nodes and display thereof. In that way it is possible to ensure reliable remote monitoring of the function of a, or also a plurality of, condensate drains. Instead of a portable query and output device, the data from the various sensor nodes can also be transferred to a stationary monitoring station by way, for example, of a data network. For example, measurement data of sensor nodes of various industrial plants at different locations can be brought together at such a monitoring station. Preferably, the energy generating device, which is preferably in the form of a thermogenerator, has associated therewith an energy storage means, by means of which it is possible to ensure a preferably constant energy supply for the electronic control unit of the sensor node.

BRIEF DESCRIPTION OF THE DRAWINGS

The invention is described in greater detail hereinafter by way of example on the basis of embodiments with reference to the accompanying Figures.

The Figures include in part simplified diagrammatic views. In part identical references are used for the same but possibly not identical elements. Various views of the same elements may be on different scales.

DETAILED DESCRIPTION

Figure 1:
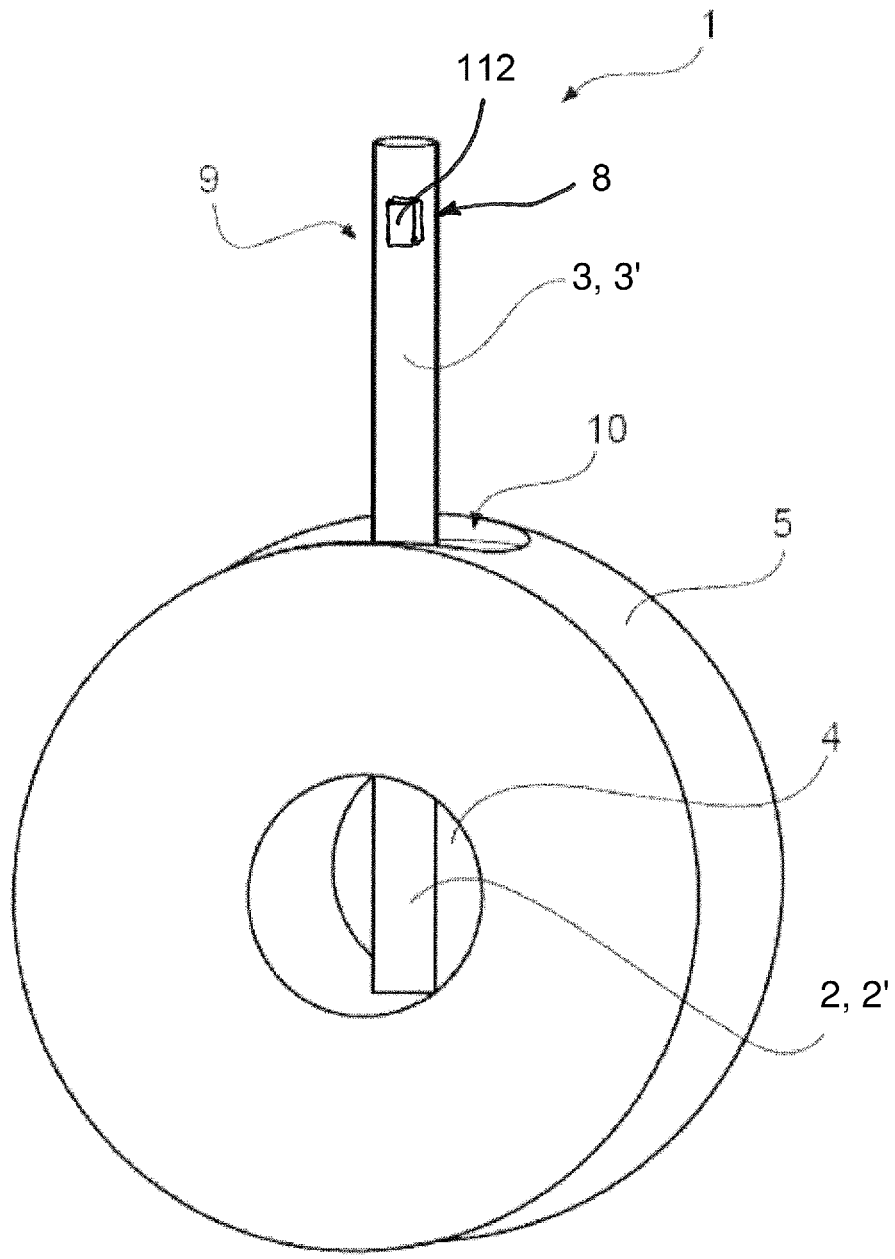
FIG. 1 shows a perspective view of a flow sensor.

FIG. 1 shows a flow sensor 1 with a vibration body 9 and a main body 5 which is of an annular configuration. In this case, the vibration body 9 is of a bar-shaped configuration and has a first region 2 and a second region 3. Provided in the main body 5 is a through passage 10 in which the vibration body 9 is arranged. The main body 5 has an opening 4 of a predetermined flow cross-section. The first region 2 of the vibration body 9 projects into the opening 4.

Alternatively, the vibration body 9 can be of such a configuration that the first region adjoins the flow cross-section for the medium, that is to say is arranged adjacent to the flow cross-section, and thus at least partially touches the flow surface. The medium, such as, for example, a multiphase flow, for example steam or vapor and condensate, flows through the predetermined cross-section of opening 4. The second region 3 projects from the main body 5 above the through passage 10. At the second region 3, a measuring location 8 is provided, at which a vibration converter 112 is arranged.

Figure 2:
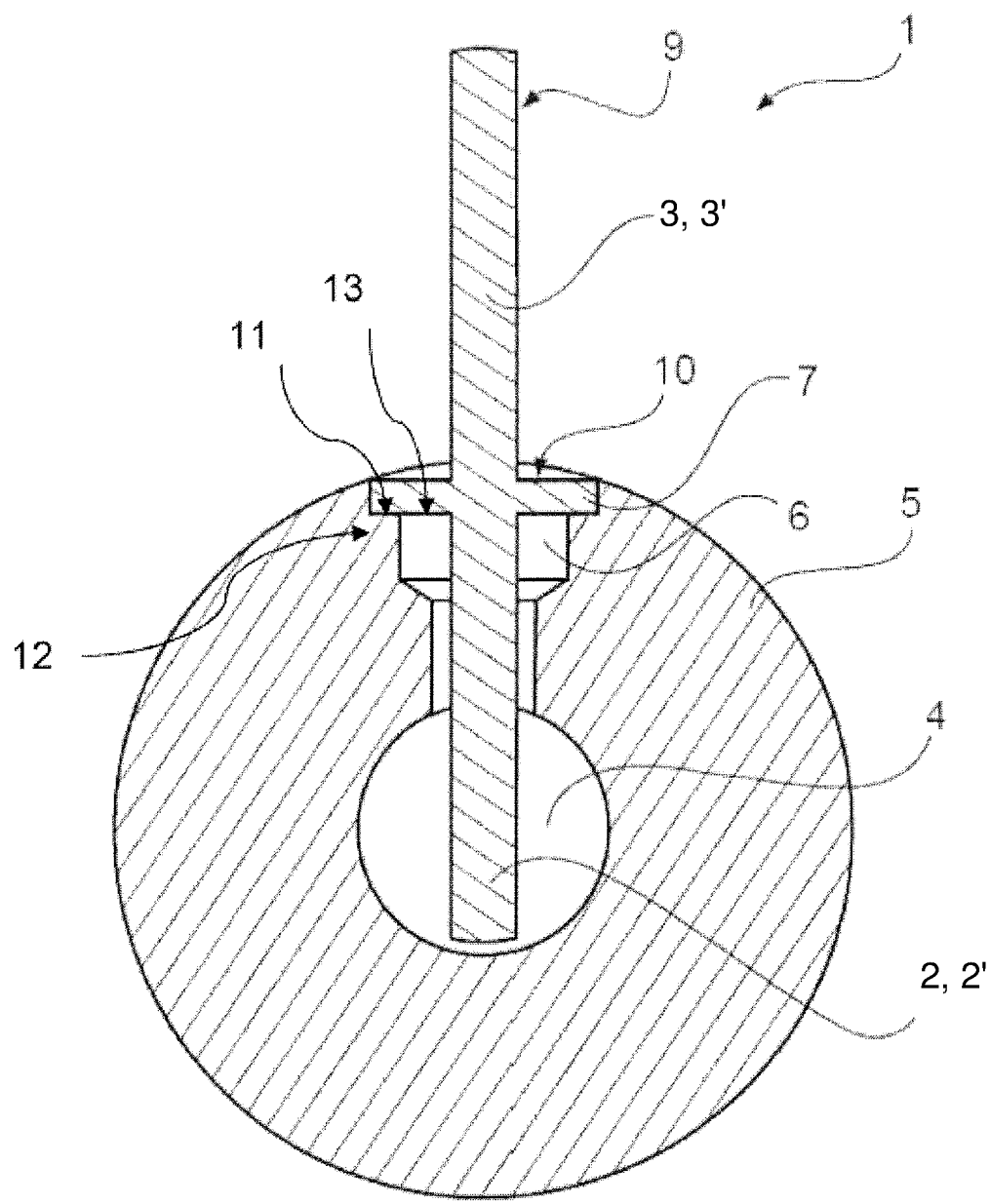
FIG. 2 shows a sectional view of the FIG. 1 flow sensor.
Figure 3:
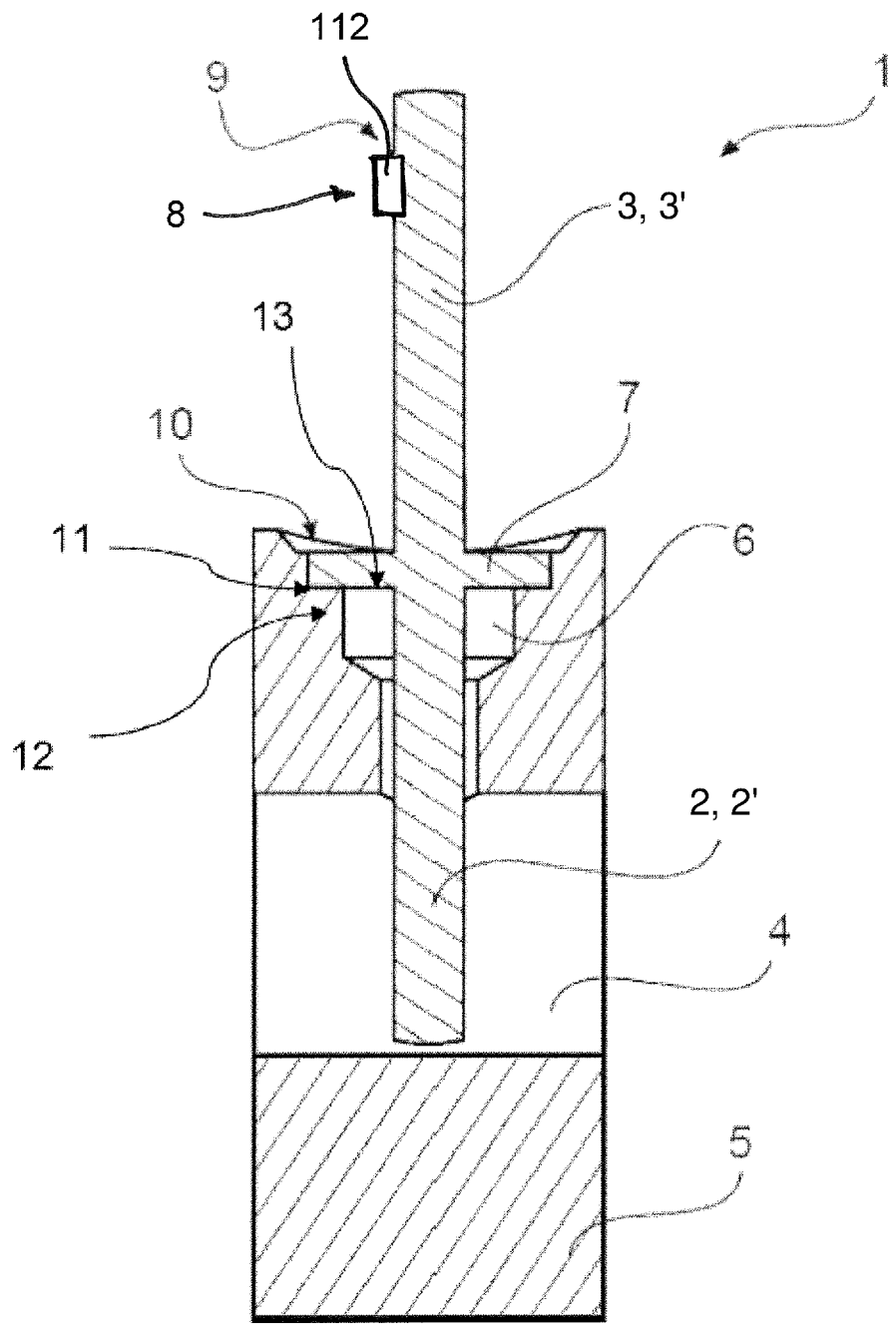
FIG. 3 shows a further sectional view of the FIG. 1 flow sensor.

FIGS. 2 and 3 show sectional views of the flow sensor 1. In addition to FIG. 1, it can be seen from FIGS. 2 and 3 that the first region 2 and the second region 3 are connected together in a connecting region 7. In this case, the connecting region 7 is of such a configuration that it was fitted through the passage 10 into the main body 5, and rests on a contact surface 11 of a shoulder 12 in a stepped bore 6. The first region 2 projects through the bore 6 into the opening 4. The second region 3 projects beyond the main body 5. The vibration body 9 has two, preferably coaxially arranged, bending beams for forming the first and second regions 2, 3 which are fixedly connected together by way of the connecting region 7 in the form of the mounting shoulder or collar 7'. The measuring location 8 at which a vibration converter 112 is arranged is provided at the second region 3 of the vibration body 9. The bending beams are preferably of a circular cross-section and are arranged on mutually opposite side faces of the mounting shoulder or collar 7'. The bending beams 2', 3' are preferably of equal diameters. The mounting shoulder or collar 7' is larger in diameter than both bending beams 2', 3'. The cylindrical mounting shoulder or collar 7' bears with a face 13 against a contact surface 11 of the main body 5. The bending beam 2 is arranged to project substantially perpendicularly at that face 13 and forms the first region of the vibration body 9 that at least partially projects into the multi-phase flow.

Figure 4:
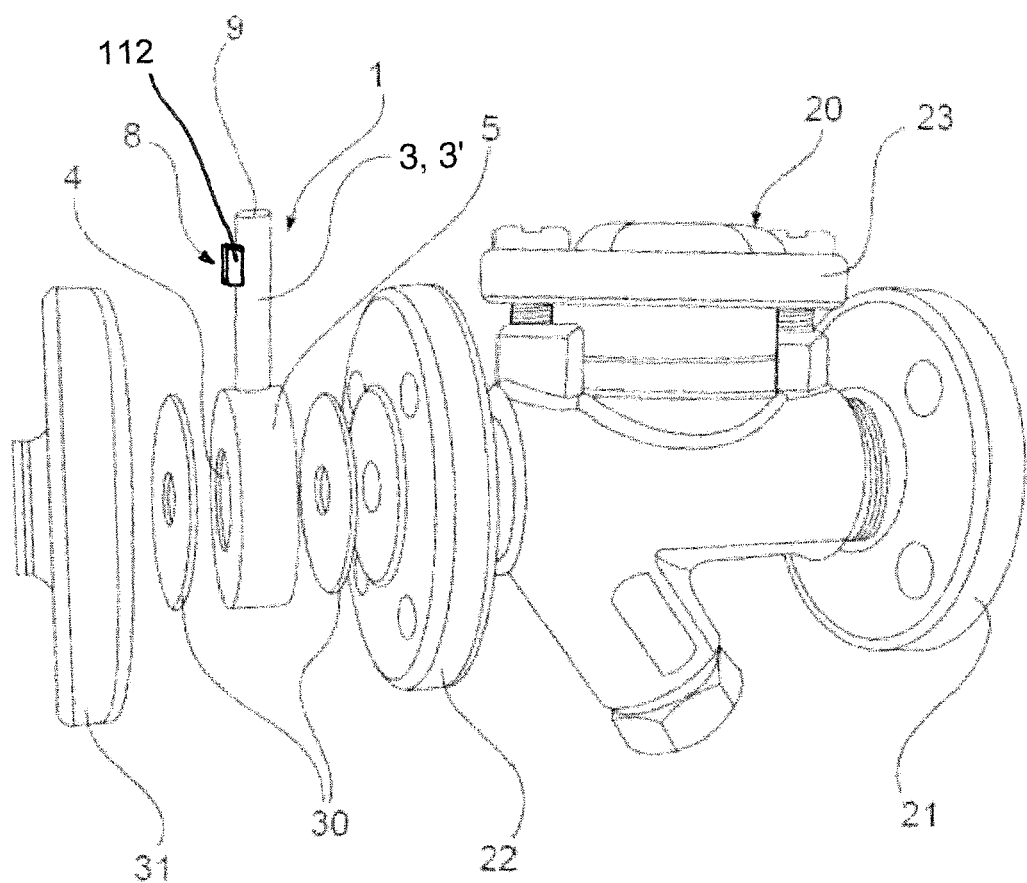
FIG. 4 shows an arrangement of a condensate drain and a flow sensor.

FIG. 4 shows the assembly of a condensate drain 20 with a flow sensor 1. In this case, the assembly of the flow sensor 1 with the condensate drain 20 is shown as an exploded view. The condensate drain 20 has a housing 23. Arranged on the housing 23 are two condensate drain flanges 21 and 22, which are usually fixed to a pipe carrying a medium. The flow sensor 1 is arranged between the condensate drain flange 22 and a pipe flange 31 provided on a pipe. A respective seal 30 is provided between the flow sensor 1 and the condensate drain flange 22 and the pipe flange. The seals 30, the condensate drain flange 22, the pipe flange 31, and the opening 4 are of a cross-section of the same size. In that respect, the cross-section is precisely as large as the cross-section of a pipe connected to the pipe flange 31.

In that way the flow properties of the medium are not altered when flowing through the opening 4 in the direction of the condensate drain 20. Accordingly, the vibrations generated by means of the vibration body 9 are those which are excited by the flow around the latter. Those vibrations are detected by the vibration converter by way of the measuring location 8 and passed to an evaluation device for evaluation of the data contained therein. When there is a plurality of flow sensors (sensor nodes) in a condensate drain system, the data can be communicated to a central control unit (base station) and passed by the latter to a control center.

Figure 5:
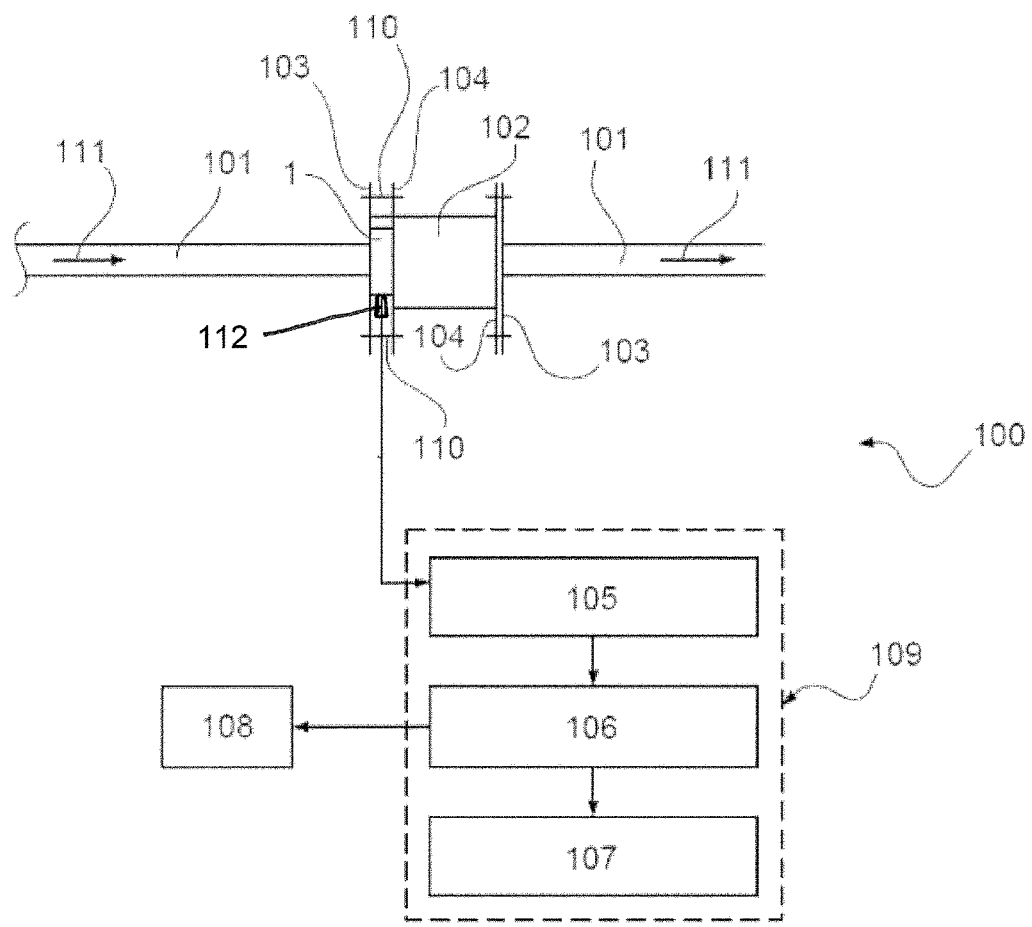
FIG. 5 shows a diagrammatic view of an embodiment of a monitoring device.

FIG. 5 diagrammatically shows a monitoring device 100. The monitoring device 100 has two pipes 101, a fitting 102, and an electronic evaluation device 109. The pipes 101 each have a respective pipe flange 103 connected to a fitting flange 104 associated with the fitting 102, by way of a releasable connection 110, in particular a screw means. The pipes 101 each carry a medium such as, for example, a multi-phase flow formed from vapor and water. A flow sensor 1 is arranged upstream of the respective fitting 102 in the flow direction 111 of the medium. In this case, the flow sensor 1 is clamped between the respective pipe flange 103 and the fitting flange 104.

The flow sensor 1 detects the flow of the medium and produces signals representative of the flow behavior. The signals are passed by way of a vibration converter 112 to the electronic evaluation device 109. The vibration converter 112 is fixedly wired or wirelessly connected to the electronic evaluation device 109. The electronic device 109 receives the signals sent to it in an input region 105 and stores them. The electronic evaluation device 109 also stores a data set 107 containing data from reference measurements of the flow. In this case such a data set 107 contains certain properties of the flow such as, for example, the condensate level and the flow speed for various operating conditions, that is to say for drainage without water hammer and with water hammer and without drainage. The data set 107 and the data from the input region 105 are processed in a step 106, that is to say compared together and evaluated. The precise operating condition, that is to say operability, the condensate amount, the vapor loss amount, and the pressure stage are precisely determined by the evaluation operation. In a further step, the results are outputted to a hand measuring device 108. Alternatively they can also be passed to a base station 108 and from there to a control center. In that case, the data can be communicated from the sensor node to the hand measuring device and/or to the base station by radio. In that way, a plurality of users can monitor the operability of each of the individual fittings 102 in the system with the background of the entire system and precisely determine same at any moment in time.

Figure 6:
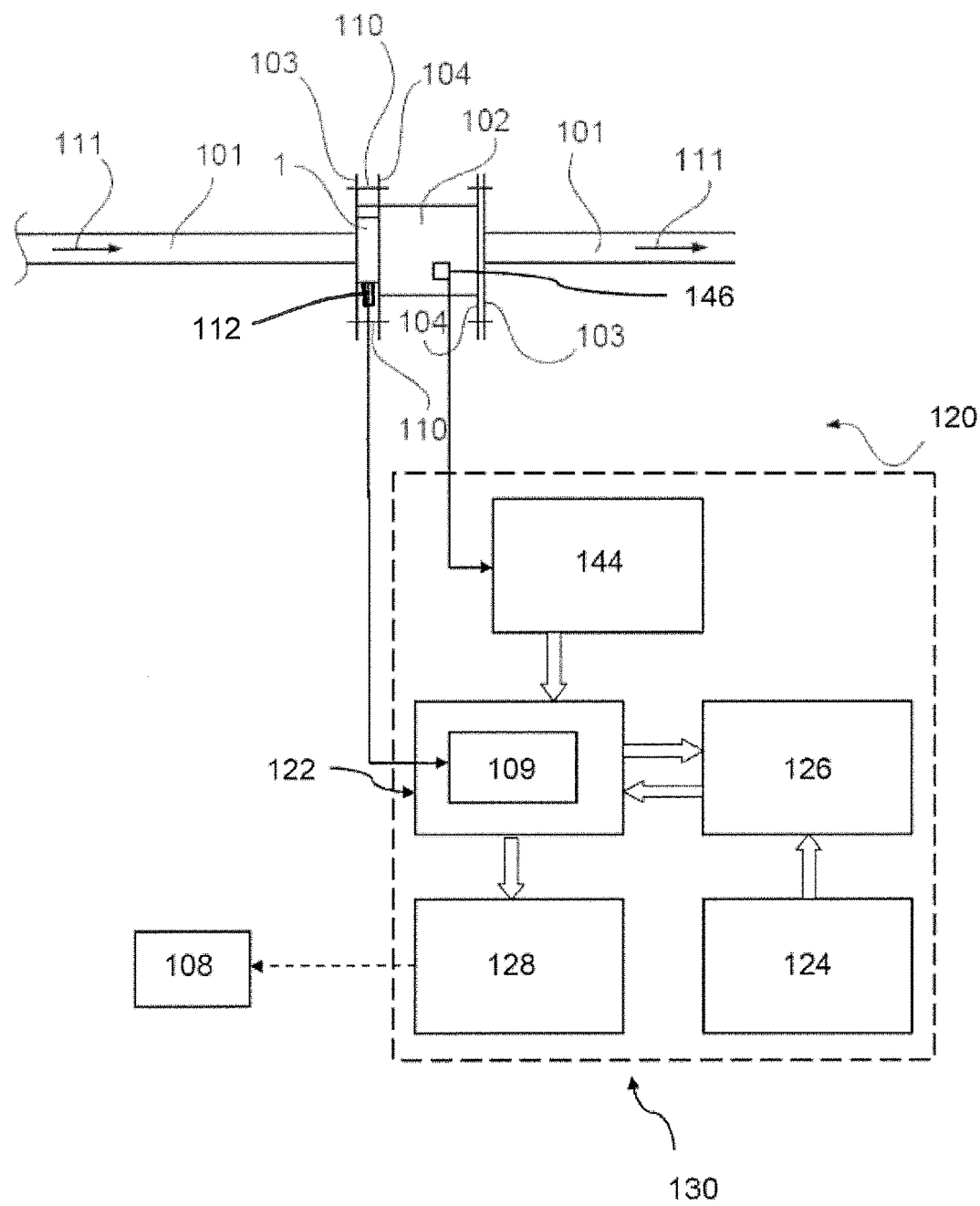
FIG. 6 shows a diagrammatic view of a further embodiment.

FIG. 6 shows a further embodiment of a diagrammatically illustrated monitoring device 120. The monitoring device 120 in turn has two pipes 101, a fitting 102, and an evaluation device 109. The evaluation device 109 is part of an electronic control unit 122, which together with an energy generating device 124, an energy storage unit 126, a communication unit 128, and a temperature measuring device 144, constitutes a sensor node 130. The sensor node is coupled in particular in a data-transfer relationship, by way of its evaluation device 109, to the vibration converter 112 and the flow sensor 1. Remote monitoring of the fitting 102 is guaranteed by means of the sensor node 130. Possible defects of the fitting 102 can be detected by the remote monitoring process both at an early stage and also easily and in particular reliably. Preferably, the data detected by the flow sensor 1 is recorded by the evaluation device 109 and preferably wirelessly communicated from the control unit 122 by way of the communication unit 128 to a base station 108 or also a portable query and output device. In addition, there is provided a temperature measuring device 144 linked to the control unit for monitoring the operating condition of the fitting 102. In the present embodiment, the temperature measuring device 144 has a temperature sensor 146 arranged on the fitting 102.

Figure 7A:
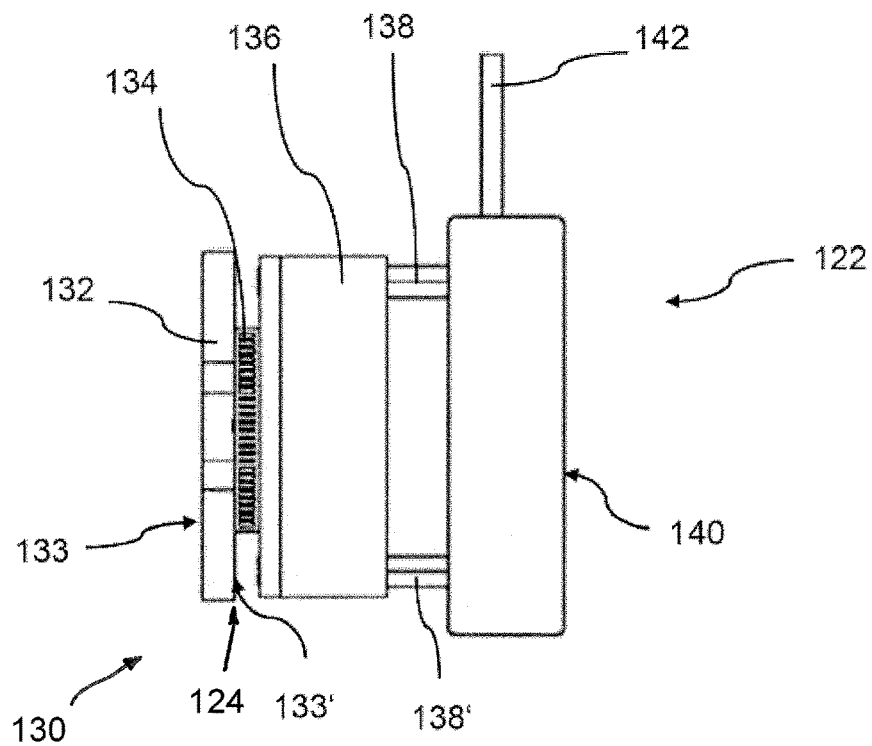
FIGS. 7a and 7b show a front view and a plan view of a sensor node according to the invention.
Figure 7B:
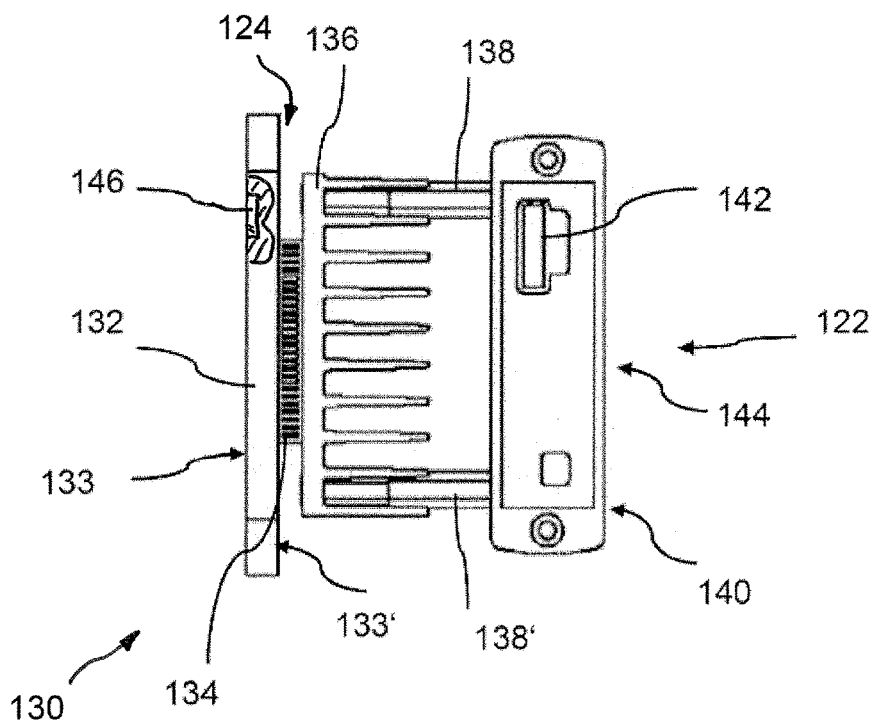

FIGS. 7a and 7b show various views of the sensor node 130. The energy generating device 124, which is preferably in the form of a thermogenerator, has a carrier plate 132 which is preferably directly fixed with a base surface 133 to a heating body like, for example, the fitting 102 to be monitored. A Peltier element 134 is arranged at the opposite base surface 133' of the carrier plate 132. Small amounts of electrical energy which are sufficient to operate the sensor node 130 are generated by means of the Peltier element 134 due to the temperature difference occurring on both sides of the Peltier element. In addition, a cooling body 136 having a plurality of cooling ribs is arranged on the Peltier element 134, by means of which the temperature difference at the Peltier element is increased and thus the effectiveness of the energy generating device 124 is improved. A housing 140 is arranged on the cooling body 136 by way of spacers 138, 138', within which housing are arranged the energy storage unit 126, the control unit 122, the temperature measuring device 144, and the communication unit 128, which together with the energy generating device 124 constitute the sensor node 130. By means of the communication unit 128 (FIG. 6), which in the present embodiment is in the form of a radio module 142, data transfer is then possible to a portable query and output device 108 or to a base station 108. From the stationary base station, the detected measurement data can be communicated to a central monitoring station which is not at the actual location of the monitoring procedure. In addition provided in the housing 140 is a temperature measuring device 144 which is coupled to a temperature sensor 146 arranged on the carrier plate.

The invention claimed is:

1. A sensor for detecting properties of a multi-phase flow of a medium, the sensor comprising:
   a main body including an opening having a cross-section configured to carry the multi-phase flow;
   a vibration body including a first region configured to project into or be adjacent to the cross-section, and a second region that is elastically coupled to the first region and configured to be outside the cross-section, the second region including a measurement location, wherein the vibration body is formed from a material with a high modulus of elasticity, and the first region and the second region include respective ends that are freely swinging by virtue of the first region being elastically coupled to the second region; and
   a vibration converter unit coupled to the measurement location and configured to convert vibrations at the measurement location into an electric signal,
   wherein the vibrations arise from direct contact between the multi-phase flow and the first region of the vibration body, and
   wherein the first region and the second region form a coupled system that couples the vibrations to the measurement location from the first region and the second region, the vibration body has a bar-shaped configuration.

2. The sensor of claim 1 wherein the cross-section is annular.

3. The sensor of claim 1 wherein the vibration body further includes a connecting region fixedly disposed on the main body and configured to elastically couple the first region to the second region and the vibration body to the main body.

4. The sensor of claim 3 wherein:
   the connecting region comprises a cylindrical mounting shoulder including a first side and a second side opposite the first side,
   the first region comprises a first bending beam having a first circular cross-section, and is connected to the first side; and
   the second region comprises a second bending beam having a second circular cross-section, and is connected to the second side.

5. The sensor of claim 4 wherein:
   a first ratio of a first diameter of the cylindrical mounting shoulder relative to a thickness of the cylindrical mounting shoulder is in a first range of 5 to 9,
   a second ratio of the first diameter relative to a second diameter of each bending beam is in a second range of 1.5 to 3.5, and
   a third ratio of a length of each bending beam relative to the second diameter is in a third range of 2 to 6.

6. The sensor of claim 1 wherein the cross-section of the main body is adapted to the cross-section of a pipe carrying the multi-phase flow to the sensor.

7. The sensor of claim 1 further comprising:
   an evaluation device electrically coupled to the vibration converter unit.

8. The sensor of claim 7 wherein the main body is located between a pipe having a first flange and a condensate drain having a second flange, and the main body is releasably connected to the pipe and the condensate drain by the first flange and the second flange.

9. The sensor of claim 7 wherein the main body is attached to a fitting, and further comprising:
   a temperature sensor attached to the fitting; and
   a temperature measuring device coupled to the temperature sensor and configured to detect a temperature of the medium,
   wherein the evaluation device is in communication with the temperature measuring device and is configured to determine whether there is a congestion of the multi-phase flow based on the temperature.

10. The sensor of claim 7 wherein the evaluation device includes a data set comprising a reference measurement of the multi-phase flow, and the evaluation device is configured to evaluate the electric signal by comparing the electric signal to the data set.

11. The sensor of claim 7 further comprising:
    an energy generating device; and
    a communication unit,
    wherein the evaluation device is configured to receive power from the energy generating device and transfer data to the communication unit.

12. A method of monitoring a condensate drain, the method comprising:
    exciting, by a multi-phase flow of a medium, a first vibration in a first region of a vibration body that is at least partially in or adjacent to the multi-phase flow, and a second vibration in a second region of the vibration body that is outside the multi-phase flow, the first vibration arising from direct contact between the multi-phase flow and the first region of the vibration body, and wherein the vibration body is formed from a material with a high modulus of elasticity;
    detecting, by a vibration converter unit at a measurement location on the second region, a third vibration comprising the first vibration and the second vibration, wherein the first region is coupled to the second region via a coupling region that is configured to elastically couple the first region to the second region and the first region and the second region include respective ends that are freely swinging by virtue of the first region being elastically coupled to the second region such that detecting the third vibration at the measurement location comprises:
    simultaneously detecting an in-phase vibration and an out-of-phase vibration of the first region and the second region at the measurement location; and
    determining, by an evaluation device, a property of the multi-phase flow based on a property of the third vibration.

13. The method of claim 12 wherein determining the property of the multi-phase flow comprises:
    recording a reference measurement of the third vibration;
    storing the reference measurement as a data set; and
    comparing a current measurement of the third vibration to the data set.

14. The method of claim 12 wherein the vibration converter unit generates a signal in response to detecting the third vibration, and determining the property of the multi-phase flow comprises:
    determining a first amplitude and a first resonance frequency of an in-phase component of the signal; and
    determining a second amplitude and a second frequency of an out-of-phase component of the signal.

15. The method of claim 14 wherein determining the property of the multiphase flow further comprises:
    determining a damping of the medium based on one or more of the first amplitude and the first resonance frequency of the in-phase component of the signal, and the second amplitude and the second frequency of the out-of-phase component of the signal; and determining the property of the multi-phase flow based on the damping.

16. The method of claim 15 wherein the property of the multi-phase flow is a condensate level of the medium, a flow speed, an operating condition, a pressure stage, a density of the medium, or a vapor loss amount.

17. The method of claim 12 wherein the vibration converter unit generates a signal in response to detecting the third vibration, the signal including one or more components each having a frequency and an amplitude, and further comprising:
  determining a relationship between the property of the multi-phase flow, and the frequency and the amplitude of at least one of the one or more components,
  wherein the property of the multi-phase flow is determined based on the relationship.

18. The method of claim 17 wherein the property of the multi-phase flow comprises an operability, a pressure stage, a condensate amount, or a vapor loss amount, and the one or more components includes a first component at a first resonance frequency having a first amplitude, and a second component at a second resonance frequency having a second amplitude.

19. A sensor for detecting properties of a multi-phase flow of a medium, the sensor comprising:
  a main body including an opening having a cross-section configured to carry the multi-phase flow;
  a vibration body configured to project into or be adjacent to the cross-section, the vibration body including a first region configured to at least partially project into the multi-phase flow of the medium and a second region configured to be outside the cross-section, the second region including a measurement location; and
  a vibration converter unit coupled to the measurement location and configured to convert vibrations at the measurement location into an electric signal,
  wherein the vibrations arise from direct contact between the multi-phase flow and the first region of the vibration body, and
  wherein the first region and the second region form a coupled system that couples the vibrations to the measurement location from the first region and the second region, and the first region and the second region include respective ends that are freely swinging by virtue of the first region being elastically coupled to the second region.

* * * * *